United States Patent [19]

Engelson

[11] Patent Number: 5,261,916
[45] Date of Patent: Nov. 16, 1993

[54] DETACHABLE PUSHER-VASOOCCLUSIVE COIL ASSEMBLY WITH INTERLOCKING BALL AND KEYWAY COUPLING

[75] Inventor: Erik T. Engelson, Mountain View, Calif.

[73] Assignee: Target Therapeutics, Fremont, Calif.

[21] Appl. No.: 806,912

[22] Filed: Dec. 12, 1991

[51] Int. Cl.$^5$ .................. A61M 29/00; A61B 17/00
[52] U.S. Cl. .................................. 606/108; 606/1; 606/191; 604/264; 604/171
[58] Field of Search ............... 623/1; 606/108, 157, 606/158, 191, 195, 1; 604/48, 52, 53, 215, 256, 264, 171; 128/838, 840

[56] References Cited

U.S. PATENT DOCUMENTS

| 4,512,338 | 4/1985 | Balko et al. .................. 606/191 |
| 4,739,768 | 4/1988 | Engelson . | |
| 4,884,579 | 12/1989 | Engelson . | |
| 4,923,464 | 5/1980 | DiPisa ........................... 606/195 |
| 4,994,069 | 2/1991 | Ritchart et al. .............. 606/191 |
| 5,037,427 | 8/1991 | Harada et al. ................ 623/1 |
| 5,108,407 | 4/1992 | Geremia et al. .............. 606/1 |

Primary Examiner—Stephen C. Pellegrino
Assistant Examiner—G. Dawson
Attorney, Agent, or Firm—Morrison & Foerster

[57] ABSTRACT

A pusher-vasoocclusive coil assembly that is advanced through a catheter to a site within a vessel and is manipulated to detach the coil from the assembly. The coil has an enlarged member at its proximal end and the pusher has a keyway at its distal end that receives the enlarged member in interlocking engagement. The pusher and coil are coupled by placing the enlarged member in the keyway and enclosing the coupled assembly with a coaxial sleeve. The coil-pusher-sleeve assembly is positioned at the site and the sleeve is retracted to allow the member to move out of the keyway to uncouple the pusher and coil.

12 Claims, 1 Drawing Sheet

DETACHABLE PUSHER-VASOOCCLUSIVE COIL ASSEMBLY WITH INTERLOCKING BALL AND KEYWAY COUPLING

TECHNICAL FIELD

The present invention is in the general field of surgical instruments and relates specifically to an apparatus for delivering a vasoocclusion coil to a selected site within a vessel (e.g., an aneurysm) via a catheter.

BACKGROUND ART

Vasoocclusion coils or wires are used to occlude a site, such as an aneurysm, within a vessel. The coils may be of a regular (e.g., helical) configuration or assume a random convoluted configuration at the site. Vasoocclusion coils are described in U.S. Pat. No. 4,994,069. The coils are normally made of a radioopaque, biocompatible metal such as platinum, gold, or tungsten. In treating aneurysms it is common to place a plurality, typically 4 to 12, coils within the aneurysm. The coils occlude the site by posing a physical barrier to blood flow and by promoting thrombus formation at the site.

The coil(s) have typically been placed at the desired site using a catheter and a pusher. The site is first accessed by the catheter. In treating peripheral or neural conditions requiring occlusion, the sites are accessed with flexible, small diameter catheters such as the catheters described in U.S. Pat. Nos. 4,739,768 and 4,813,934. The catheter may be guided to the site through the use of guidewires (see U.S. Pat. No. 4,884,579) and/or flow-directed means such as balloons at the distal end of the catheter. Once the site has been accessed, the catheter lumen is cleared (i.e., the guidewire is removed if a guidewire has been used), and the coil is placed in the proximal end of the catheter and advanced through the catheter with a pusher. Pushers are wires having a distal end that is adapted to engage and push the coil distally as the pusher is advanced through the catheter. When the coil reaches the distal end of the catheter it is plunged therefrom by the pusher into the vessel. This technique of plunging the coil from the distal end of the catheter has undesirable limitations. First, because of the plunging action, the positioning of the coil at the site cannot be controlled to a fine degree of accuracy. Second, once plunged from the catheter, it is difficult to reposition or retrieve the coil if desired. Indeed, another device, called a retriever, must be threaded through the catheter to snare the coil to reposition or retrieve it.

In view of these limitations, techniques have recently been developed to enable more accurate placement of coils within a vessel. In one technique (described in U.S. patent application Serial No. 492,717, filed 13 March 1990) the coil is bonded via a metal-to-metal joint to the distal end of a pusher made of a different metal than the coil. The coil-carrying pusher is advanced through the catheter to the site and a low electrical current is passed through the pusher-coil assembly. The current causes the joint between the pusher and coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a given time period so that rapid detachment of the coil from the pusher is not possible. In another technique the confronting ends of the pusher and coil are designed such that the pusher clamps onto the wire and holds it until the clamp is released. Accordingly, this methodology utilizes a mechanical detachment mechanism rather than an electrolytic mechanism.

A primary object of the present invention is to provide an alternative mechanical means for detaching a vasoocclusive coil from a pusher at a desired vessel site.

DISCLOSURE OF THE INVENTION

One aspect of the invention is a detachable pusher-vasoocclusive coil assembly for use in occluding a selected site within a vessel comprising in combination: (a) a vasoocclusive coil that carries an enlarged member at its proximal end; (b) a pusher having a keyway at its distal end that receives the enlarged member in interlocking engagement; and (c) means carried coaxially about the pusher and coil that is axially movable relative to the pusher and coil from a first position at which the means encloses the member interlocked within the keyway to maintain the member within the keyway to a second position at which the means does not enclose the interlocked member and keyway and the member is free to withdraw from the keyway and thus uncouple the pusher and coil.

Another aspect of the invention is a method for occluding a selected site within a vessel comprising the steps of: (a) accessing the site with a distal end of a catheter; (b) advancing the above-described assembly through the catheter with the member interlocked within the keyway to a position distally of the distal end of the catheter; (c) permitting the member to withdraw from the keyway and thereby detach the coil from the pusher; and (d) withdrawing the catheter and pusher from the vessel.

Figure 1:
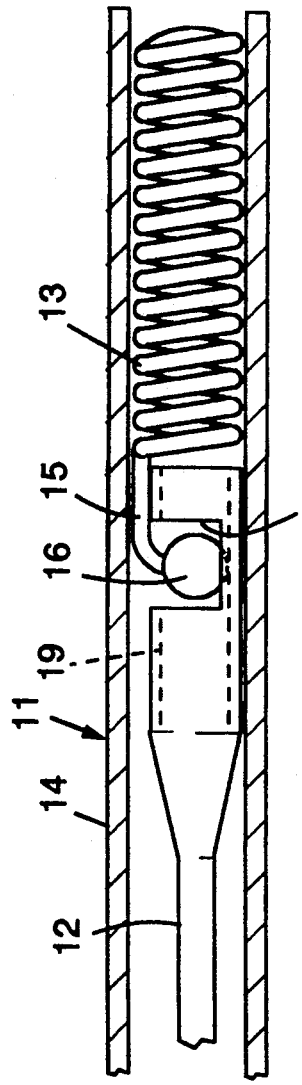
FIG. 1 is an enlarged, sectional elevational view of an embodiment of the pusher-vasoocclusive coil assembly of the invention showing the pusher and coil coupled.

In the drawings proximal is left and distal is right. Only the distal portions of certain elements of the assembly are depicted in the drawings.

MODES FOR CARRYING OUT THE INVENTION

The assembly, generally designated 11, shown in the drawing comprises three principal parts: (a) a pusher 12; (b) a vasoocclusive coil 13; and (c) a sleeve 14.

Coil 13 is shown in FIG. 1 as a uniform diameter helical coil wire. It may, however, have another regular configuration or have a random configuration. In any event, the coil must be dimensioned to be able to be advanced through a catheter that is sized to access the desired site. The coil is made of a radioopaque, biocompatible metal such as platinum, gold or tungsten so that its location within the vessel may be viewed radiographically.

For use in occluding peripheral or neural sites the coils will typically be made of 0.05 to 0.15 mm diameter platinum wire that is wound to have an inner diameter of 0.15 to 0.96 mm with a minimum pitch (i.e., the windings are close or tight). The length of the wire (wound) will normally be in the range of 0.5 to 60 cm, preferably 2 to 20 cm. As indicated, if desired, the coil may be formed so that the coil takes an essentially linear configuration in which it may be advanced through the catheter and assume a randomly oriented relaxed condition after it is released from the catheter (see U.S. Pat. No. 4,994,069).

Figure 2:
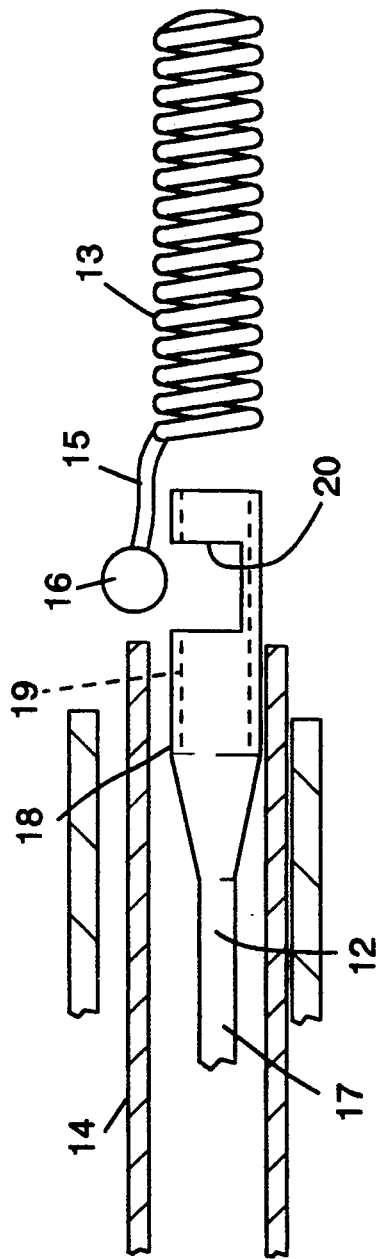
FIG. 2 is an enlarged sectional view of the assembly of FIG. 1 and a catheter showing the pusher and coil uncoupled.
Figure 3:
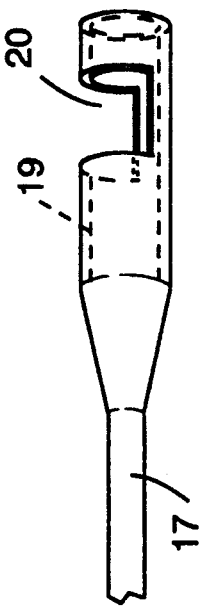
FIG. 3 is an enlarged perspective view of the distal end of the pusher of FIG. 1.

A proximal segment 15 of the coil (or a separate wire affixed to the proximal end of the coil) is deformed so that it extends proximally of the windings of the coil. The tip of segment 15 carries a sphere or ball 16. The ball may be positioned centrally relative to the segment or be offset from the axis of the segment. The length of segment 15 will normally be 0.25 to 1.2 mm and the diameter of ball 16 will normally be 0.2 to 1 mm. Segment 15 should be deformable so that ball 16 may be manipulated into engagement with the pusher as described below. Further, it is preferred that segment 15 be normally biased radially so that it will assume the position shown in FIG. 2 when not constricted.

Pusher 12 comprises a proximal end segment (not shown) that provides the means by which the pusher may be gripped and manipulated, a main central core 17 and an enlarged cylindrical tip 18. Tip 18 has an axial bore 19 of at least about the diameter of ball 16 and a radial slot or keyway 20 that intersects bore 19 and has dimensions that are adapted to receive ball 16. If desired the tip may also have an axial slot extending from its distal end to the radial keyway that is dimensioned to receive segment 15. The outer diameter of tip 18 is dimensioned to be slidably received within the lumen of the enclosing means and to permit segment 15 and ball 16 to be positioned within keyway 20. (See FIG. 1.)

The entire length of the pusher will be such as to be capable of being advanced entirely through the catheter 21 to the vessel site with a sufficient portion of the proximal end of the pusher protruding from the proximal end of the catheter to enable the pusher to be manipulated. Typically, the core segment will constitute at least about 90-95% of the entire length of the pusher. For use in peripheral or neural surgeries, the pusher will normally be about 100 to 200 cm in length, more usually 160 to 180 cm in length. The diameter of the core 17 of the pusher will typically be in the range of 0.25 to 0.90 mm.

The ball 16 is maintained within the keyway by radially enclosing it. The means for coaxially enclosing the thus coupled pusher and coil may be the inner wall of the catheter that is used to access the site. However, if (a) the catheter is too elastic radially to maintain the engagement or (b) it is desired to maintain the engagement distally of the distal end of the catheter, a separate sleeve 14 that is received coaxially about the coil and pusher may be employed.

The outer diameter of sleeve 14 is such that the sleeve can be advanced through the lumen of catheter 21. Correspondingly, the inner diameter of the sleeve is sized such that it can receive the coil and pusher in coupled relationship and be able to move axially relative thereto. For use in peripheral and neural surgeries the inner diameter of the sleeve will typically be 0.3 to 1 mm. The sleeve may be made of flexible plastics that can be navigated through the catheter 21.

Assembly 11 is used to place one or more vasoocclusive coils at a selected site in a vessel as follows. The pusher and coil are assembled as shown in FIG. 1 with the ball 16 within keyway 20. If a sleeve is used to enclose the ball and keyway, the coupled assembly is inserted into the sleeve 14. Catheter 21 is inserted and navigated through the vessel lumen (not shown) to the site to be occluded (e.g., on an aneurysm, vascular malformation, or arteriovenous fistula). As indicated previously, conventional catheter insertion and navigational procedures involving guidewire and/or flow-directed means may be used to access the site with the catheter. Once the distal end of the catheter is positioned at the site (its location may be determined by coating the distal end of the catheter with a radioopaque material or otherwise affixing such a material to the distal end of the catheter), the catheter is cleared (i.e., if a guidewire has been used to position the catheter, it is withdrawn from within the catheter) and the pusher and coil assembly 11 is advanced through the catheter. (See FIG. 2.) The assembly is advanced distally of the distal end of the catheter so that the ball and keyway are free of the catheter with the coil positioned exactly at the desired site. If a sleeve is used, the sleeve is then retracted (moved axially in the proximal direction) so that it no longer encloses the keyway and ball. The radial bias exerted by the wire 15 causes the ball 16 to move out of the keyway and the coil to be uncoupled from the pusher. (See FIG. 2.) It will be appreciated that it is not essential that the wire 15 exert a radial bias and that the uncoupling may be achieved simply by gravity or fluid flow at the site. If additional coils need to be placed at the site, the pusher and sleeve are withdrawn and the procedure is repeated. After the desired number of coils have been placed at the site, the catheter is withdrawn from the vessel.

Modifications of the above-described modes for carrying out the invention that are obvious to those of skill in the mechanical and surgical instrument design arts and related fields are intended to be within the scope of the following claims.

I claim:

1. A detachable pusher-vasoocclusive coil assembly for use in occluding a selected site within a vessel comprising in combination:
   (a) a vasooclusive coil having a proximal end and a distal end and which carries an enlarged member at its proximal end;
   (b) a pusher having a proximal end and a distal end and a radial keyway at its distal end that receives the coil's enlarged member in interlocking engagement; and
   (c) means carried coaxially about the pusher and coil that is axially movable relative to the pusher and coil from a first position at which the means encloses the member interlocked within the keyway to maintain the member within the keyway to a second position at which the means does not enclose the interlocked member and radial keyway and the member is free to withdraw from the radial keyway and thus uncouple the pusher and coil.

2. The assembly of claim 1 wherein the means is a catheter.

3. The assembly of claim 1 wherein the means is a sleeve adapted to be received within a catheter.

4. The assembly of claim 1 wherein the enlarged member is carried on the proximal end of a wire that extends proximally from the coil.

5. The assembly of claim 1 wherein the enlarged member is generally spherical in shape.

6. The assembly of claim 1 wherein the pusher has a cylindrical distal tip.

7. The assembly of claim 1 wherein the keyway includes an axial slot extending from the distal end of the pusher to the radial keyway.

8. A method for occluding a selected site within a vessel comprising the steps of:
   (a) accessing the site with the distal end of a catheter;
   (b) advancing the assembly of claim 1 through the catheter with the member interlocked within the radial keyway to a position distally of the distal end of the catheter;
   (c) permitting the member to withdraw from the radial keyway and thereby detach the coil from the pusher; and
   (d) withdrawing the catheter and pusher from the vessel.

9. A method for occluding a selected site within a vessel comprising the steps of:
   (a) accessing the site with the distal end of a catheter;
   (b) advancing the assembly of claim 3 through the catheter with the sleeve in the first position so as to position the coil at the site with the interlocked member and radial keyway distally of the distal end of the catheter;
   (c) moving the sleeve to the second position whereby the member may withdraw from the radial keyway and thereby detach the coil from the pusher; and
   (d) withdrawing the catheter, pusher, and sleeve from the vessel.

10. A method for occluding a selected site within a vessel comprising the steps of:
    (a) accessing the site with the distal end of a catheter;
    (b) advancing the assembly of claim 4 through the catheter with the member interlocked within the radial keyway to a position distally of the distal end of the catheter;
    (c) permitting the member to withdraw from the radial keyway and thereby detach the coil from the pusher; and
    (d) withdrawing the catheter and pusher from the vessel.

11. A method for occluding a selected site within a vessel comprising the steps of:
    (a) accessing the site with the distal end of a catheter;
    (b) advancing the assembly of claim 5 through the catheter with the member interlocked within the radial keyway to a position distally of the distal end of the catheter;
    (c) permitting the member to withdraw from the radial keyway and thereby detach the coil from the pusher; and
    (d) withdrawing the catheter and pusher from the vessel.

12. A method for occluding a selected site within a vessel comprising the steps of:
    (a) accessing the site with the distal end of a catheter;
    (b) advancing the assembly of claim 7 through the catheter with the member interlocked within the radial keyway to a position distally of the distal end of the catheter;
    (c) permitting the member to withdraw from the radial keyway and thereby detach the coil from the pusher; and
    (d) withdrawing the catheter and pusher from the vessel.

* * * * *